United States Patent [19]

Hum et al.

[11] Patent Number: 4,806,346

[45] Date of Patent: Feb. 21, 1989

[54] METHOD FOR ISOLATION OF ANTIGEN SPECIFIC IMMUNOGLOBULIN

[75] Inventors: Wah-tung Hum, Jeffersonville; Shaw-guang Lee, Villanova, both of Pa.

[73] Assignee: American Home Products Corporation, New York, N.Y.

[21] Appl. No.: 942,313

[22] Filed: Dec. 16, 1986

[51] Int. Cl.[4] .................... A61K 39/395; C12P 21/00; C07K 3/22; C07K 3/28
[52] U.S. Cl. .................................. 424/85.8; 424/101; 530/388; 530/414; 530/416; 435/68
[58] Field of Search ................. 424/85, 101; 530/388, 530/414, 416; 435/68

[56] References Cited

U.S. PATENT DOCUMENTS

| | | | |
|---|---|---|---|
| 2,669,559 | 2/1954 | Reid | 530/416 |
| 4,136,094 | 1/1979 | Condie | 530/364 |
| 4,302,384 | 11/1981 | Funatsu et al. | 424/85 |
| 4,341,762 | 7/1982 | Haast | 424/88 |
| 4,675,384 | 6/1987 | Dromard et al. | 530/380 |

OTHER PUBLICATIONS

Xie et al., cited in Biol. Abstracts 68, 1978 Ref. No. 9207.
Cope, cited in Chem. Abstracts vol. 92:116317n 1980.
Goch et al., cited in Chem. Abstracts vol. 92:56611s 1980.

Primary Examiner—Ronald W. Griffin
Assistant Examiner—Jacqueline M. Stone
Attorney, Agent, or Firm—George Tarnowski

[57] ABSTRACT

A process for preparing the purified $F(ab)_2$ fragment of equine Ig(T) from horses hyperimmunized with snake venom which comprises:
(a) passing crude diluted hyperimmune equine serum contianing snake venom antigen specific Ig(T) buffered to an acidic pH through a strong base anion exchange polymer;
(b) passing the resultant pass-through solution to which is added sodium chloride to a concentration of 0.05–0.124M through a strong acid cation exchange polymer;
(c) adjusting the pH of the pass-through of step (b) to a pH of 3.3, and digesting said pass-through with pepsin; and
(d) ultrafiltering said pepsin-digested pass-through to obtain purified $F(ab)_2$ fragment of the snake venom antigen specific equine Ig(T).

16 Claims, No Drawings

METHOD FOR ISOLATION OF ANTIGEN SPECIFIC IMMUNOGLOBULIN

The present invention is directed to a method for the purification and isolation of the F(ab)$_2$ fragment of snake antigen specific immunoglobulin produced by hyperimmunized horses.

The accepted primary therapeutic course of treatment of snake envenomation is based primarily on the intravenous administration of antivenin, which is commercially prepared serum derived from horses immunized against venom of a particular species or variety of species of snake. Thus, for example, the commercially available Antivenin [Crotalidae] Polyvalent (ACP), produced by Wyeth Laboratories, Inc., is an antivenin produced from the serum of horses immunized against the venom of four species of snakes: *Crotalus adamanteus* (eastern diamondback rattlesnake), *Crotalus atrox* (western diamondback rattlesnake), *Crotalus terrificus* (tropical rattlesnake) and *Bothrops atrox* (fer-de-lance).

Equine source antivenin is essentially the horse serum fraction which contains antibodies to the protein antigens which have been injected into the horse, i.e. the snake venoms. This equine serum fraction has been found to have an electrophoretic mobility intermediate between those of the γ- and β-globulins and which has been designated Ig(T) [van der Scheer and Wyckoff, *Proc. Soc. Exp. Biol. Med.*, 43, 427 (1940)]. This type of Ig is barely detectable in normal serum, but increases considerably in the serum of horses strongly immunized with protein antigens, such as diphtheria or tetanus toxoid or snake venoms [Weir and Porter, *Biochem. J.*, 100, 63 (1966)]. Studies of the physical nature of native Ig molecules have shown that they are folded into 6–7 domains. The F(ab)$_2$ domains in the N-terminal region of the protein chain are responsible for the antigen binding activity and thus the antivenom activity of the equine-source antivenin. The Fc domains in the C-terminal region mediate the effector function of the Ig molecule. This latter portion of the Ig, which is not required for the venom neutralization process, is considered to be responsible, at least in part, for the induction of serum sickness in snakebite victims who are treated with equine-source antivenins.

The use of equine-source antivenins in the treatment of envenomation is attended by undesirable side effects. Since it is often difficult to determine the amount of antivenin required to deal with the effects of the venom, it is necessary to inject significant amounts of antivenin into the victim. Since the antivenin is a mixture of equine serum protein, including the whole Ig(T) molecule, injection of antivenin results in the administration into a human of significant amounts of a foreign protein, including the Fc portion of the equine Ig molecules. As a result, some patients may develop serum sickness marked by urticarial rashes, edema, adenitis, joint pains, high fever and prostration, while other patients may develop anaphylactic shock. Moreover, in addition to containing contaminating horse proteins, Ig molecules which do not take part in venom neutralization and the undesirable Fc portion of the Ig molecule, antivenin may also contain bacterial endotoxins, which also contribute to the side effects of antivenin therapy.

Accordingly, it has become apparent that a more highly purified immunopharmacological agent useful in the treatment of envenomation and not attended by sensitivity reactions is highly desirable. Efforts to purify equine-source antivenin have been directed to utilizing chromatographic principles. However, the methods employed to date are unsatisfactory for a number of reasons. Thus, Goudswaard et al., *Immunochemistry*, 14, 717 (1977), have used hydrophobic interaction chromatography with phenyl-Sepharose CL-4B in the presence of ammonium sulfate to isolate Ig(T) from equine serum. However, extensive pre-treatment of the whole serum is necessary to achieve satisfactory results from the hydrophobic interaction chromatography process. Thus, the whole serum is first subjected to delipidation, dialysis, salting out and redialysis before the serum is finally subjected to hydrophobic interaction chromatography. Moreover, obtention of nearly completely purified Ig(T) requires refractionation of the partially purified Ig(T) on the phenyl-Sepharose CL-4B column. So, while the entire procedure is capable of yielding purified Ig(T), it does so at the cost of a long and laborious multistep procedure incorporating an ammonium sulfate precipitation step, which is not only expensive and can result in loss of neutralizing Ig(T), but can also coprecipitate many other serum proteins.

In another Ig(T) purification process, Russell et al., *Am. J. Trop. Med. Hyg.*, 34 (1), 141 (1985), equine-source antivenin is purified by polyacrylamide gel affinity chromatography. According to this procedure, use is made of the antigen-antibody complexing principle, so that a polyacrylamide gel is prepared which incorporates snake venom into the matrix of the gel. A solution of the hyperimmune equine-source serum containing antivenin is placed in contact with the prepared gel. The desired Ig(T) component is selectively adsorbed into the appropriate and specific binding sites of the venom incorporated into the gel matrix. The extraneous and undesired proteins associated with equine-source antivenin remain unbound, and are washed away. The Ig(T) bound to the gel matrix is then recovered by eluting the gel with a desorbing agent. This process, while less laborious than the hydrophobic interaction chromatography process, is still quite costly. Lyophilized snake venom, which is used to prepare the venom/gel matrix is very expensive and the quantities needed to prepare commercial levels of purified antivenin would make this method uneconomical. Moreover, handling lyophilized snake venom requires the utmost caution to prevent accidental envenomation through open wounds or cuts.

A particularly significant aspect of the two processes discussed is the fact that they yield purified, whole Ig(T), thus including the Fc portion which is not required for venom neutralization and which is implicated in inducing serum sickness and anaphylactic shock. Thus, although purified, the Ig(T) obtained by the prior art processes still has the potential to cause adverse sensitivity reactions.

Therefore, it would be desirable to have a simple, efficient and economic process for purifying equine-source antivenin, which not only removes extraneous and undesired foreign proteins and endotoxins, but also isolates the neutralizing F(ab)$_2$ portion of the Ig(T) molecule, while removing the undesired Fc portion. The present invention is directed to such a process, which is simple, inexpensive, is readily expandable to commercial scale operations and provides an antivenin comprising substantially the F(ab)$_2$ portion of Ig(T) and having a three-to-fourfold increase in the specific activity of antivenin.

According to the process of the invention, crude diluted hyperimmune equine serum containing snake venom antigen specific Ig(T) is buffered to an acidic pH (e.g. pH 5.1) and passed through a strong base anion exchange polymer; to the resulting pass-through solution is added sodium chloride to a concentration of 0.05-0.125M and the salinized solution is passed through a strong acid cation-exchange polymer; the pass-through from the cation exchange polymer is concentrated, the pH adjusted to low pH (e.g. 3.1) and the resulting concentrate digested with pepsin; and the digested concentrate is purified by hollow fiber filtration having a molecular weight cut-off of 50-75K to yield purified F(ab)$_2$ fragment of the equine Ig(T).

The process of the invention can be employed to isolate and purify the F(ab)$_2$ fragment of equine Ig(T) which is obtained from horses which have been hyperimmunized with venom from any desired snake species. All envenomation by pit vipers in North, Central and South America can be treated by an antivenin prepared from the venoms mentioned earlier, i.e. venoms for *Crotalus adamanteus, C. atrox, C. terrificus* and *Bothrops atrox*. Accordingly, an all-purpose pit viper antivenin for the designated geographic area can be prepared using venoms from these snakes. Envenomation by snakes with a cobra-like venom, for example, by the North American coral snake, must be treated with antivenin made from hyperimmunized serum obtained by use of the appropriate snake species venom. In like manner, specific and unique antivenins can be prepared by the process of the invention using serum obtained by use of the requisite snake venom.

The process for obtaining hyperimmunized serum from horses is well-established and conventional, and a brief discussion of the process can be found in Criley, "Development of a Multivalent Antivenin for the Family Crotalidae," an article in *Venom*, Amer. Ass. for Advance. of Sci., 1956.

According to the process of the invention, hyperimmunized equine-source serum is diluted 5-10 times with acetate buffer to achieve an acidic pH of about 5. The resultant diluted and buffered serum is passed through a strong base anion-exchange polymer. An especially preferred strong base anion exchange polymer is DEAE-cellulose having a high surface area, a rigid structure capable of withstanding the pressures generated by high liquid flow rates, autoclavability and regenerability. One such product is the Zeta Prep® DEAE Cartridge commercially produced by American Fluid Conditioning Co. However, any strong base anion exchange polymer meeting the above-outlined requirements is suitable for use in the claimed process.

The pass-through from the strong base anion exchange polymer results in a buffered serum solution that is substantially albumin-free Ig(T) from which most contaminating proteins are also removed. The anion exchange polymer can be regenerated by conventional methods known in the art. To the substantially albumin-free Ig(T) containing pass-through is added sodium chloride to achieve a concentration of 0.05-0.125M. An especially preferred sodium chloride concentration is 0.05-0.10M. The correct sodium chloride concentration ensures an optimal recovery of Ig(T) in the next step.

The sodium chloride-treated pass-through solution is then passed through a strong acid cation exchange polymer which is capable of separating high molecular weight molecules. A particularly preferred strong acid cation exchange polymer is the sulfopropyl dextran product Zeta Prep® SP-Cartridge also produced by American Fluid Conditioning Company. The pass-through solution from the strong acid cation exchanger is purified Ig (60-70% Ig(T)). The pass-through solution can be concentrated by hollow fiber filtration or through pellicon membrane. The pH is then adjusted to about 3.3 with acetic acid and 0.05-0.1% pepsin (enzyme:substrate) is added to the concentrated pass-through. The pepsin is allowed to digest the Ig(T) for about 16 hours at 37° C. to yield a solution containing F(ab)$_2$ and Fc fragments and the pepsin.

The F(ab)$_2$ fragment can be purified by hollow fiber filtration through a hollow fiber membrane having a molecular weight cut-off at 50-75K. Any polymeric hollow open fiber material capable of ultrafiltration to provide 100% rejection of material in 50,000-75,00 molecular weight range is suitable. The recovered F(ab)$_2$ fragment can then be formulated into a final "antivenin" dosage form according to conventional procedures used in preparing antivenin by methods known in the art.

The strong acid cation and strong base anion exchange polymers can both be regenerated by washing with 1.0M sodium chloride, followed by equilibration in acetate buffer.

The procedure outlined above can be carried out on a batch scale wherein the ion exchange polymers are packed into chromatography columns. Similarly, the procedure can be carried out in a continuous production scale by using a suitable number of packed columns in each of the two chromatography steps, with continuous column regeneration in order to maintain a continuous sequence of chromatographic separations. The continuous production of purified F(ab)$_2$ gives a production rate that is three times faster than the ammonium sulfate precipitation method currently being employed. The latter method is a long and laborious procedure consuming very large quantities of ammonium sulfate. The elimination of this step alone, along with the capability of producing highly purified F(ab)$_2$ fragment from Ig(T) provides an extremely significant advance in the state of the antivenin production art.

EXAMPLE 1

One liter of hyperimmune horse serum from horses immunized with venom from *Crotalus adamenteus, C. atrox, C. terrificus* and *Bothrops atrox* is diluted with 5 liters of acetate buffer (50 mM sodium acetate, 20 mM acetic acid, pH 5.0). The dilute buffered serum is passed through a 3.2 liter Zeta Prep® DEAE Cartridge column at a flow rate of 350 ml/minute at room temperature. The pass through, which is substantially free of albumin and high molecular weight contaminants, is collected and to it is added enough sodium chloride to obtain a final concentration of 0.08M. The latter is then passed through a 3.2 liter Zeta Prep® SP-Cartridge column at a flow rate of 350 ml/minute at room temperature. The pass-through obtained in this step is enriched Ig(T) (60-70%). This pass-through is concentrated to 1 liter (by hollow fiber filtration or pellicon membrane filtration), and the pH is adjusted to 3.3 with acetic acid. Protein concentration is determined by the method of Lowry.

To the pH 3.3-adjusted pass-through is added 0.05% pepsin (enzyme pepsin to substrate Ig(T) ratio) and it is digested for 16 hours at 37° C. The digested pass-through is then filtered through a hollow fiber or pellicon membrane to filter out the Fc fragment and pepsin.

The SP-Cartridge column is regenerated by washing with 5 liter of 1.0M sodium chloride followed by equilibration in acetate buffer.

The pharmacological evaluation of the F(ab)₂ fragment obtained according to the procedure of the invention is set forth in Table 1. In this Table, one dose is defined as the amount of sample that will neutralize a minimum of 198 $LD_{50}$'s of *C. atrox* venom, 1452 $LD_{50}$'s of *C. terrificus* venom and 858 $LD_{50}$'s of *B. atrox* venom. Potency is the number of $LD_{50}$'s of venom that is neutralized by 200 mg/ml of the sample. The skin test results are a measurement of anaphylaxis caused by foreign antigen. In this procedure, the test animal (guinea pig or rabbit) is first sensitized with horse serum. Two weeks later, sample is injected into the animal to test for the development of anaphylaxis activity as manifested by skin rashes and edema. The entries "+++++" and "+++" represent a strong, and moderately strong, anaphylactic reaction, respectively, while "– – –" denotes absence of any anaphylactic activity.

TABLE 1

|   | Total Protein (mg/ml) | Protein Recovery % | gm/dose | Potency $LD_{50}$/ml | Skin Test |
|---|---|---|---|---|---|
| horse serum* | 70 | 100 | | | +++++ |
| (NH₄)₂SO₄ precip.** | 50 | 71 | 1.6 | 30 | +++ |
| Enriched Ig(T)*** | 33 | 47 | 0.9 | 50 | |
| F(ab)₂ | 20 | 28 | 0.5 | 95 | – – – |

*refers to horse serum obtained from horses immunized with snake venom.
**refers to commercially available Antivenin [Crotalidae] Polyvalent (ACP) obtained by the conventional ammonium sulfate precipitation method.
***refers to whole Ig(T) purified from hyperimmunized horse serum as described herein.

The results in Table 1 show that the F(ab)₂ fragment of Ig(T) from hyperimmunized horse serum has very significantly improved neutralizing capability and potency when compared to both conventionally prepared antivenin and enriched Ig(T), and at the same time does not give rise to any anaphylactic activity such as occurs with the conventionally prepared antivenin.

What is claimed is:

1. A process for preparing the purified F(ab)₂ fragment of equine Ig(T) from horses hyperimmunized with snake venom which comprises:
   (a) passing crude diluted hyperimmune equine serum containing snake venom antigen specific Ig(T) buffered to an acidic pH through a strong base anion exchange polymer;
   (b) passing the resultant pass-through solution to which is added sodium chloride to a concentration of 0.05–0.125M through a strong acid cation exchange polymer;
   (c) adjusting the pH of the pass-through of step (b) to 3.3, and digesting said pass-through with pepsin; and
   (d) ultrafiltering said pepsin-digested pass-through to obtain purified F(ab)₂ fragment of the snake venom antigen specific equine Ig(T).

2. The process of claim 1, wherein the hyperimmunized equine serum is derived from horses hyperimmunized with a combination of venoms derived from *Crotalus adamanteus*, *C. atrox*, *C. terrificus* and *Bothrops atrox*.

3. The process of claim 1, wherein said crude hyperimmune serum is diluted 5–10 times with acetate buffer to a pH of about 5.0.

4. The process of claim 1 wherein said strong base anion exchange polymer is diethylaminoethyl cellulose.

5. The process of claim 1, wherein said strong base anion exchange pass-through is salinized to a sodium chloride concentration of 0.08M.

6. The process of claim 1, wherein said strong acid cation exchange polymer is sulfopropyl dextran.

7. The process of claim 1, wherein said strong acid cation exchange polymer pass-through is adjusted to a pH of about 3.3 with acetic acid.

8. The process of claim 1, wherein the strong acid cation exchange polymer pass-through is digested with pepsin for about 16 hours at 37° C.

9. The process of claim 8, wherein said pepsin is used at a concentration of 0.05% on an enzyme to substrate basis.

10. The process of claim 1, wherein said ultrafiltration is carried out using a hollow fiber filter having a molecular weight cut-off of 50,000–75,000.

11. The process of claim 1, wherein said strong base anion exchange polymer is regenerated using 1M sodium chloride followed by equilibration in acetate buffer.

12. The process of claim 1, wherein said strong acid cation exchange polymer is regenerated by washing with 1.0M sodium chloride followed by equilibration in acetate buffer.

13. The process of claim 1, which is carried out continuously on regenerable ion exchange polymer columns.

14. A process for preparing the purified F(ab)₂ fragment of equine Ig(T) from horses hyperimmunized with snake venom which comprises:
   (a) passing crude hyperimmune equine serum, containing snake venom antigen specific Ig(T) buffered to a pH of about 5.0 with acetate buffer, through a strong base diethylaminoethyl-cellulose anion exchange column;
   (b) passing the resultant pass-through solution, to which is added sodium chloride to a concentration of about 0.08M, through a strong acid sulfopropyl dextran cation exchange column;
   (c) adjusting the pH of the pass-through of step (b) to about 3.3 with acetate buffer, and digesting said pass-through with 0.05% pepsin for 16 hours at 37° C.; and
   (d) ultrafiltering said pepsin-digested pass-through using a hollow fiber filter having a molecular weight cut-off of 50,000–75,000 to obtain purified F(ab)₂ fragment of the snake venom antigen specific equine Ig(T).

15. A snake envenomation antivenin comprising the purified F(ab)₂ fragment of equine Ig(T) from horses hyperimmunized with snake venom prepared by the process of claim 1 and a pharmaceutically acceptable carrier.

16. The antivenin of claim 15, which is lyophilized and reconstitutable for parenteral administration.

* * * * *